(12) United States Patent
Kwon et al.

(10) Patent No.: US 11,266,357 B2
(45) Date of Patent: Mar. 8, 2022

(54) BIO-SIGNAL FEATURE SCALING APPARATUS AND METHOD

(71) Applicant: SAMSUNG ELECTRONICS CO., LTD., Suwon-si (KR)

(72) Inventors: Ui Kun Kwon, Hwaseong-si (KR); Chang Soon Park, Chungju-si (KR); Dae Geun Jang, Yongin-si (KR); Young Soo Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1088 days.

(21) Appl. No.: 15/833,727

(22) Filed: Dec. 6, 2017

(65) Prior Publication Data

US 2018/0177465 A1    Jun. 28, 2018

(30) Foreign Application Priority Data

Dec. 28, 2016 (KR) .......................... 10-2016-0181374

(51) Int. Cl.
| | | |
|---|---|---|
| *A61B 5/021* | (2006.01) | |
| *A61B 5/00* | (2006.01) | |
| *A61B 5/11* | (2006.01) | |
| *A61B 5/08* | (2006.01) | |
| *A61B 5/0205* | (2006.01) | |
| *A61B 5/316* | (2021.01) | |

(Continued)

(52) U.S. Cl.
CPC ............ *A61B 5/7278* (2013.01); *A61B 5/021* (2013.01); *A61B 5/0205* (2013.01); *A61B 5/02108* (2013.01); *A61B 5/0816* (2013.01); *A61B 5/1102* (2013.01); *A61B 5/316* (2021.01); *A61B 5/318* (2021.01); *A61B 5/389* (2021.01); *A61B 2560/0223* (2013.01)

(58) Field of Classification Search
CPC .................. A61B 5/021–02141; A61B 5/0295
See application file for complete search history.

(56) References Cited

U.S. PATENT DOCUMENTS

| | | | |
|---|---|---|---|
| 6,361,501 B1 * | 3/2002 | Amano | A61B 5/02028 600/485 |
| 6,527,725 B1 * | 3/2003 | Inukai | A61B 5/02125 600/485 |
| 8,597,195 B2 | 12/2013 | Gallant et al. | |

(Continued)

FOREIGN PATENT DOCUMENTS

| | | |
|---|---|---|
| JP | 4388585 B2 | 12/2009 |
| KR | 10-1503604 B1 | 3/2015 |
| KR | 10-2016-0108081 A | 9/2016 |

OTHER PUBLICATIONS

Yoon et al., "Nonconstrained Blood Pressure Measurement by Photoplethysmography", Journal of the Optical Society of Korea, vol. 10, No. 2, Jun. 15, 2006, pp. 91-95.

(Continued)

*Primary Examiner* — Meredith Weare
(74) *Attorney, Agent, or Firm* — Sughrue Mion, PLLC (57) ABSTRACT

A bio-signal feature scaling apparatus may include: a processor configured to execute instructions to: extract a feature from a bio-signal of an object; estimate a cause of change in a bio-state of the object; calibrate a scale factor based on the estimated cause of change in the bio-state; and scale the extracted feature by applying the calibrated scale factor to the extracted feature.

17 Claims, 10 Drawing Sheets

(51) Int. Cl.
 *A61B 5/318* (2021.01)
 *A61B 5/389* (2021.01)

(56) References Cited

U.S. PATENT DOCUMENTS

| | | | |
|---|---|---|---|
| 9,161,699 B2 | 10/2015 | Heller | |
| 9,162,065 B2 | 10/2015 | Karst et al. | |
| 9,289,133 B2 | 3/2016 | Cohen et al. | |
| 2005/0027205 A1* | 2/2005 | Tarassenko | A61B 5/0816 600/529 |
| 2013/0130215 A1* | 5/2013 | Bock | G16H 20/17 434/247 |
| 2014/0031638 A1 | 1/2014 | Jung et al. | |
| 2014/0187941 A1* | 7/2014 | Shusterman | A61B 8/04 600/438 |
| 2015/0031965 A1 | 1/2015 | Visvanathan et al. | |
| 2015/0073250 A1 | 3/2015 | Goor et al. | |
| 2016/0051156 A1 | 2/2016 | Kim et al. | |
| 2016/0058300 A1 | 3/2016 | Yoon et al. | |
| 2016/0256116 A1 | 9/2016 | Baik et al. | |
| 2016/0270668 A1 | 9/2016 | Gil | |
| 2017/0172431 A1* | 6/2017 | Kim | A61B 5/02125 |
| 2017/0340920 A1* | 11/2017 | Posio | G09B 5/02 |
| 2017/0360314 A1* | 12/2017 | Proenca | A61B 5/02125 |
| 2018/0235567 A1* | 8/2018 | Bezemer | A61B 5/02416 |
| 2018/0263570 A1* | 9/2018 | Chen | A61B 5/7278 |
| 2018/0279965 A1* | 10/2018 | Pandit | A61B 5/7225 |
| 2018/0353088 A1* | 12/2018 | Nakazawa | A61B 5/7207 |

OTHER PUBLICATIONS

Millasseau et al., "The Vascular Impact of Aging and Vasoactive Drugs: Comparison of Two Digital Volume Pulse Measurements", American Journal of Hypertension, vol. 16, No. 6, Jun. 2003, pp. 467-472, doi:10.1016/S0895-7061(03)00569-7.

* cited by examiner

BIO-SIGNAL FEATURE SCALING APPARATUS AND METHOD

CROSS-REFERENCE TO RELATED APPLICATION(S)

This application claims the priority from Korean Patent Application No. 10-2016-0181374, filed on Dec. 28, 2016, in the Korean Intellectual Property Office, the entire disclosure of which is incorporated herein by reference for all purposes.

BACKGROUND

1. Field

Apparatus and method consistent with example embodiments relate to a bio-signal feature scaling apparatus and method.

2. Description of Related Art

Healthcare technology has been gaining attention due to the rapid entry into an aging society and social problems such as increase in medical expenses. Accordingly, not only medical devices that may be utilized by hospitals and inspection agencies but also portable small-sized medical devices such as wearable devices are being developed. In addition, such portable small-sized medical device may be worn by a user in the form of a wearable device capable of directly measuring cardiovascular health status such as blood pressure or the like, to enable the user to directly measure and manage the user's cardiovascular health status.

Therefore, recently, studies on a method and apparatus to estimate a health status such as a blood pressure by analyzing a bio-signal with a portable small-sized device have been conducted.

SUMMARY

One or more example embodiments provide a bio-signal feature scaling apparatus and method.

According to an aspect of an example embodiment, there is provided a bio-signal feature scaling apparatus including a processor configured to execute instructions to: extract a feature from a bio-signal of an object; estimate a cause of change in a bio-state of the object; calibrate a scale factor based on the estimated cause of change in the bio-state; and scale the extracted feature by applying the calibrated scale factor to the extracted feature.

The bio-signal may include at least one from among an electrocardiogram signal, a photoplethysmogram signal, an electromyogram signal, and a ballistocardiogram signal.

The cause of change in the bio-state may include at least one from among breath-holding, anaerobic exercise, aerobic exercise, and stress.

The processor may be further configured to measure a breathing pattern comprising a respiration rate of the object and estimate the cause of change in the bio-state based on the measured breathing pattern.

The processor may be further configured to the breathing pattern of the object using a respiration sensor attached to the object.

The processor may be further configured to measure the breathing pattern of the object by analyzing the bio-signal.

The processor may be further configured to measure the breathing pattern of the object by analyzing a heart rate or inter beat interval (IBI) obtained from the bio-signal, or analyzing at least one from among a low frequency fluctuation component comprising an amplitude component of the bio-signal.

The processor may be further configured to calibrate the scale factor based on a model that defines a relationship between a cause of change in a bio-state and calibration of a scale factor.

According to another aspect of an example embodiment, there is provided a bio-signal feature scaling method including: extracting a feature from a bio-signal of an object; estimating a cause of change in bio-state of the object; calibrating a scale factor based on the estimated cause of change in the bio-state; and scaling the extracted feature by applying the calibrated scale factor to the extracted feature.

The bio-signal feature scaling method, wherein the bio-signal may include at least one from among an electrocardiogram signal, a photoplethysmogram signal, an electromyogram signal, and a ballistocardiogram signal.

The bio-signal feature scaling method, wherein the cause of change in the bio-state may include at least one from among breath-holding, anaerobic exercise, aerobic exercise, and stress.

The bio-signal feature scaling method, wherein the estimating of the cause of change in the bio-state comprises measuring a breathing pattern comprising a respiration rate of the object and estimating the cause of change in the bio-state based on the measured breathing pattern.

The bio-signal feature scaling method, wherein the measuring of the breathing pattern may include measuring the breathing pattern of the object using a respiration sensor attached to the object.

The bio-signal feature scaling method, wherein the measuring of the breathing pattern may include measuring the breathing pattern of the object by analyzing the bio-signal.

The bio-signal feature scaling method, wherein the measuring of the breathing pattern may include measuring the breathing pattern of the object by analyzing a heart rate or inter beat interval (IBI) obtained from the bio-signal, or analyzing at least one from among a low frequency fluctuation component comprising an amplitude component of the bio-signal.

The bio-signal feature scaling method, wherein the calibrating of the scale factor may include calibrating the scale factor based on a model that defines a relationship between a cause of change in a bio-state and calibration of a scale factor.

According to another aspect of an example embodiment, there is provided a bio-signal feature scaling apparatus including: a processor configured to execute instructions to: extract a plurality of features from a bio-signal of an object; estimate a cause of change in a bio-state of the object; calibrate weights to be applied to the features, respectively, based on the estimated cause of change in the bio-state; combine the plurality of features by applying the calibrated weights to the respective features; calibrate a stored scale factor based on the estimated cause of change in the bio-state; and scale the combined plurality of features by applying the calibrated scale factor to the combined feature.

The bio-signal may include at least one from among an electrocardiogram signal, a photoplethysmogram signal, an electromyogram signal, and a ballistocardiogram signal.

The processor may be further configured to measure a breathing pattern comprising a respiration rate of the object and estimate the cause of change in the bio-state based on the measured breathing pattern.

The processor may be further configured to calibrate the weights to be applied to the features, respectively, using a model that defines a relationship between a cause of change in bio-state and calibration of a combining coefficient.

BRIEF DESCRIPTION OF THE DRAWINGS

The above and/or other aspects will become apparent and more readily appreciated from the following detailed description of example embodiments, taken in conjunction with the accompanying drawings, in which like reference numerals refer to like elements, and wherein.

DETAILED DESCRIPTION

The following detailed description is provided to assist the reader in gaining a comprehensive understanding of the methods, apparatuses and/or systems described herein according to one or more example embodiments. Various changes, modifications, and equivalents of the systems, apparatuses and/or methods described herein will suggest themselves to those of ordinary skill in the art, and it is to be understood that the example embodiments are not intended to limit the present disclosure to particular modes of practice, and it is to be appreciated that all modification, equivalents, and alternatives that do not depart from the spirit and technical scope of the present disclosure are encompassed in the present disclosure. In the following description, a detailed description of known functions and configurations incorporated herein will be omitted.

Throughout the drawings and the detailed description, unless otherwise described, the same drawing reference numerals will be understood to refer to the same elements, features, and structures. The relative size and depiction of these elements may be exaggerated for clarity, illustration, and convenience It should be noted that in some alternative implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

The terms used in the present specification are used for the purpose of describing the example embodiments, and not for the purpose of limiting and/or restricting the present disclosure. Therefore, in the following example embodiments, unless specifically defined, the meanings of terms should be interpreted based on general meanings recognized by those skilled in the art.

As used herein, the singular forms are intended to include the plural forms as well, unless the context clearly indicates otherwise. It will be further understood that the terms "comprises" and/or "comprising," or "includes" and/or "including" when used in this description, specify the presence of stated features, numbers, steps, operations, elements, components or combinations thereof, but do not preclude the presence or addition of one or more other features, numbers, steps, operations, elements, components or combinations thereof.

It will also be understood that the elements or components in the following description are discriminated in accordance with their respective main functions. In other words, two or more elements may be made into one element or one element may be divided into two or more elements in accordance with a subdivided function. Additionally, each of the elements in the following description may perform a part or whole of the function of another element as well as its main function, and some of the main functions of each of the elements may be performed exclusively by other elements. Each element may be realized in the form of a hardware component, a software component, and/or a combination thereof.

Meanwhile, an apparatus for providing a health status of the cardiovascular system described herein may be implemented as a software module or in the form of a hardware chip and be mounted in an electronic device. In this case, the electronic device may include a mobile phone, a smart phone, a notebook computer, a personal digital assistant (PDA), a portable multimedia player (PMP), a navigation system, an MP3 player, a digital camera, a wearable device, etc., and the wearable device may include various types of wearable devices, such as a wristwatch type, a wristband type, a ring type, a belt-type, a necklace type, an ankle band type, a thigh band type, a forearm band type, and the like. However, the electronic device is not limited to the above mentioned examples, and the wearable device is also not limited to the above-described examples.

Figure 1:
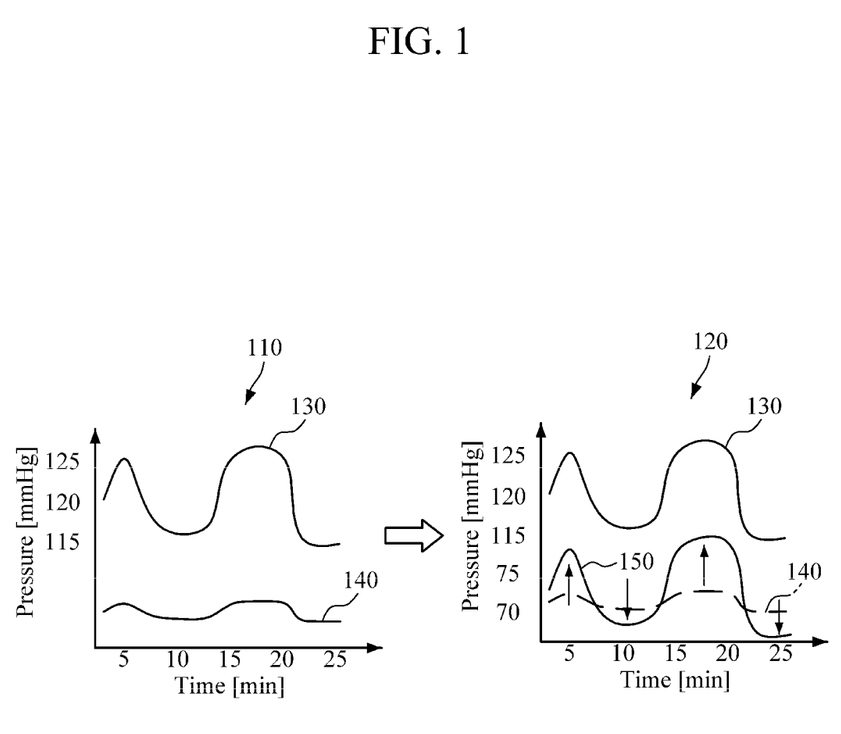
FIG. 1 is a diagram for describing a blood pressure trend tracking method according to an example embodiment.

FIG. 1 is a diagram for describing a blood pressure trend tracking method according to an example embodiment. According to an example embodiment, the blood trend tracking method may use a pulse wave analysis (PWA) technique which analyzes a photoplethysmogram (PPG) signal and estimates a blood pressure. Since the PWA is a technique that does not directly measure a blood pressure, unlike a cuff sphygmomanometer, it may not be easy to estimate the absolute value of an object's blood pressure, but it may be possible to estimate the trend of change in blood pressure, that is, a trend of increasing/decreasing blood pressure of a specific object. The blood pressure trend tracking method may consist of largely two processes of: (1) extracting a feature, that corresponds to the trend of change in blood pressure, from a PPG signal; and (2) scaling the feature to map the amount of change in the extracted feature to the amount of change in blood pressure.

A graph 110 of FIG. 1 shows an example process of extracting a feature from the PPG signal, and a graph 120 shows a process of scaling the amount of change in feature to map it to the amount of change in blood pressure according to an example embodiment.

Referring to the graph 110, a feature 140 extracted from the PPG signal increases as a reference blood pressure 130 increases, and decreases as the reference blood pressure 130 decreases. However, the graph 110 shows that there is a discrepancy between the amount of change in feature 140 and the amount of change in reference blood pressure 130.

Referring to the graph 120, when the feature 140 is scaled so that the fluctuation of feature 140 is mapped to the fluctuation of the reference blood pressure 130, it may be possible to estimate the amount of change in reference blood pressure 130 from the scaled feature 150.

The process of scaling the feature 140 to map the fluctuation of the feature 140 to the fluctuation of the reference blood pressure 130 includes a process of estimating a scale factor. A method of estimating a scaling factor according to an example embodiment may include (1) a statistics-based universal scaling factor estimation method, (2) a statistics-based custom scale factor estimation method, and (3) a calibration-based scale factor estimation method.

The statistics-based universal scale factor estimation method is a method that simultaneously measures a reference blood pressure and a feature used to estimate a blood pressure and obtain a scale factor by statistically analyzing the relationship between the reference blood pressure and the feature. The statistics-based universal scale factor estimation method may be more convenient for a user because a calibration process using a separate reference sphygmomanometer is unnecessary when a user uses a sphygmomanometer, but an error of the scale factor may increase for an outlier user who falls outside of the statistics. In addition, causes of blood pressure change may vary, and when the cause of blood pressure change changes, the scale factor may also change within individuals. The statistics-based universal scale factor estimation method may not accurately reflect an individual's cause of change in blood pressure.

The statistics-based custom scale factor estimation method is a method which obtains a customized scale factor by applying personal information of a user (e.g., height, age, weight, sex, blood pressure, vascular health, etc.) to a scale factor obtained using a statistics-based universal scale factor estimation method. The statistics-based custom scale factor estimation method may reduce an error of scale factor which occurs to the outlier user who falls outside the statistics, but like the statistics-based universal scale factor estimation method, it may not accurately reflect an individual's cause of blood pressure change.

The calibration-based scale factor estimation method is a method in which an individual user directly extracts a scale factor between a blood pressure and a feature by simultaneously measuring a reference blood pressure and the feature that corresponds to the trend of change in blood pressure. The calibration-based scale factor estimation method may allow the calibration of a scale factor through the continuous blood pressure measurement, but it may not be applied to a small-sized device capable of non-intrusive calibration and blood pressure measurement because a reference sphygmomanometer is needed for a reference blood pressure measurement and perform the calibration process.

Figure 2:
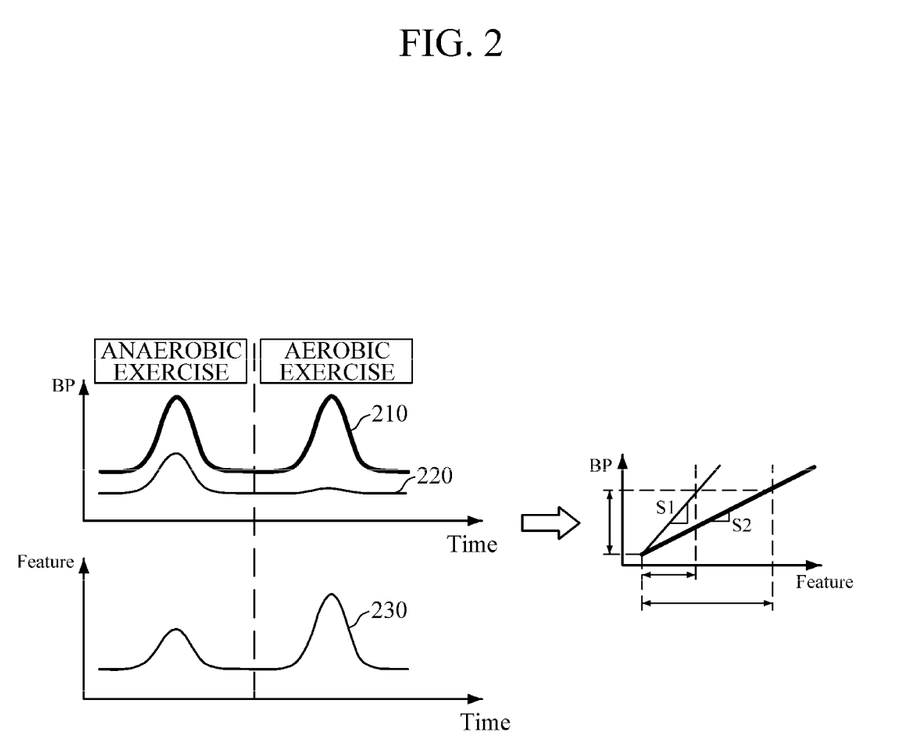
FIG. 2 illustrates example graphs showing trends of changes in a blood pressure, a feature, and a difference in scale factors according to a cause of blood pressure change according to an example embodiment.

FIG. 2 illustrates example graphs showing trends of changes in a blood pressure, a feature, and a difference in scale factors according to a cause of blood pressure change according to an example embodiment. FIG. 2 shows a blood pressure change trend, a feature change trend, and a scale factor during an anaerobic exercise and a blood pressure change trend, a feature change trend, and a scale factor during an aerobic exercise.

Referring to FIG. 2, trends of changes in the systolic blood pressure (SBP) 210 and a diastolic blood pressure (DBP) 220 during anaerobic exercise differ from trends of changes in the SBP 210 and the DBP 220 during aerobic exercise. Specifically, both the SBP and the DBP 220 rise during the anaerobic exercise, whereas during the aerobic exercise, the SBP 210 rises, but the DBP 220 does not change significantly.

In addition, the amount of change in a feature 230 (e.g., heart rate) during the aerobic exercise is greater than the amount of change in the feature 230 during the anaerobic exercise, and thus, a scale factor S1 during the anaerobic exercise may be greater than a scale factor S2 during the aerobic exercise.

That is, to increase the accuracy of blood pressure trend tracking, the scale factor needs to be calibrated according to a cause of change in the blood pressure (e.g., anaerobic exercise/aerobic exercise).

Figure 3:
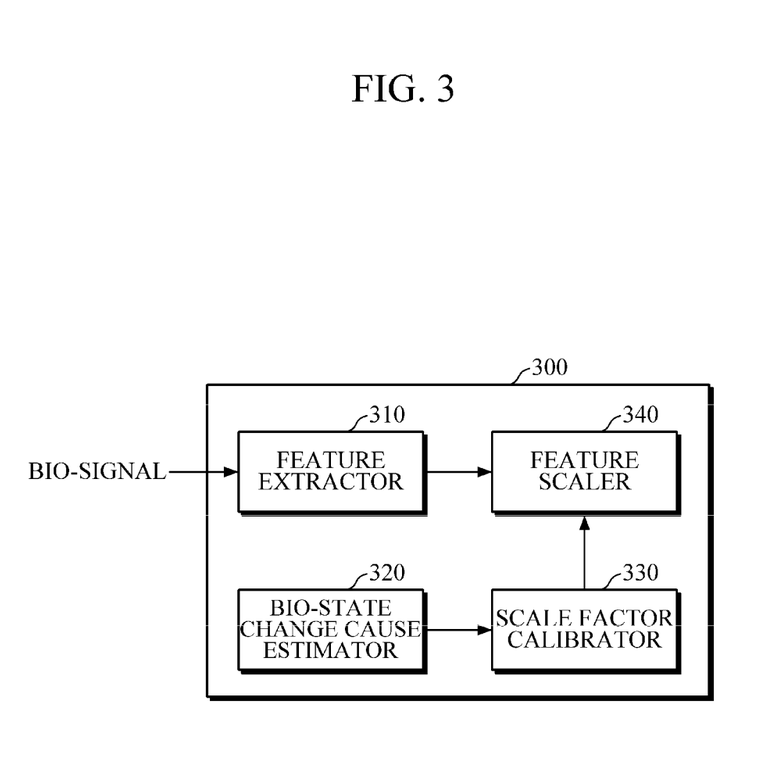
FIG. 3 is a block diagram illustrating a bio-signal feature scaling apparatus according to an example embodiment.

FIG. 3 is a block diagram illustrating a bio-signal feature scaling apparatus according to an example embodiment.

Referring to FIG. 3, the bio-signal feature scaling apparatus 300 according to an example embodiment may include a feature extractor 310, a bio-state change cause estimator 320, a scale factor calibrator 330, and a feature scaler 340.

The feature extractor 310 extracts a feature that corresponds to the change of bio-state from a bio-signal of an object. In this case, the bio-signal may be an electrical signal transmitted between cells in vivo and may include an electrocardiogram (ECG) signal, a PPG signal, an electromyogram (EMG) signal, a ballistocardiogram (BCG) signal, etc. In addition, the bio-state may include various vital signs including, for example, a blood pressure.

The bio-state change cause estimator 320 may estimate a cause of change in the bio-state of the object. Here, the cause of change in the bio-state may include breath-holding, anaerobic exercise, aerobic exercise, stress, and the like.

According to an example embodiment, the bio-state change cause estimator 320 may measure a breathing pattern including a respiration rate of the object, and estimate a cause of change in the bio-state on the basis of the measured breathing pattern. In this case, the bio-state change cause estimator 320 may estimate the cause of change in the bio-state using a model (respiration-cause relation model) which defines the relationship between the breathing pattern and the cause of change in the bio-state. The respiration-cause relation model may be established in advance using various model creation mechanisms (e.g., machine learning) and be stored in advance in an internal database or an external database of the bio-signal feature scaling apparatus 100.

The bio-state change cause estimator 320 may use various methods of measuring the breathing pattern of the object.

According to an example embodiment, the bio-signal change cause estimator 320 may directly measure the breathing pattern of the object using a respiration sensor attached to the object.

According to an example embodiment, the bio-signal change cause estimator 320 may indirectly measure the breathing pattern of the object by analyzing a bio-signal, such as an ECG signal, a PPG signal, an EMG signal, or a BCG signal. For example, the bio-state change cause estimator 320 may indirectly measure the breathing pattern of the object by analyzing a low frequency fluctuation component, i.e., an amplitude component, or the heart rate or inter beat interval (IBI) obtained from the bio-signal.

According to an example embodiment, the bio-state change cause estimator 320 may measure the breathing pattern of the object using both the respiration sensor and the bio-signal.

The scale factor calibrator 330 may calibrate the previously stored scale factor on the basis of the cause of change in the bio-state. In this case, the scale factor represents a ratio between the change in the feature and the change in the bio-state, and may be either experimentally or theoretically derived and stored in advance in the internal database or external database of the bio-signal feature scaling apparatus 100.

According to an example embodiment, the scale factor calibrator 330 may calibrate the previously stored scale factor using a model (cause-scale factor calibration relation model) which defines a relationship between the cause of change in the bio-state and the calibration of the scale factor. In this case, the cause-scale factor calibration relation model may be established in advance using various model creation mechanisms (e.g., machine learning) and may be stored in advance in the internal database or the external database of the bio-signal feature scaling apparatus 100.

The feature scaler 340 may scale the feature by applying the calibrated scale factor to the feature.

By doing so, the bio-signal feature scaling apparatus 300 may adaptively change the scale factor of the feature to be used for bio-state trend tracking according to various causes of change in the bio-state, and accordingly, it may be possible to more accurately monitor various bio-states, such as blood pressure, using the operations of the bio-signal feature scaling apparatus 300.

Figure 4:
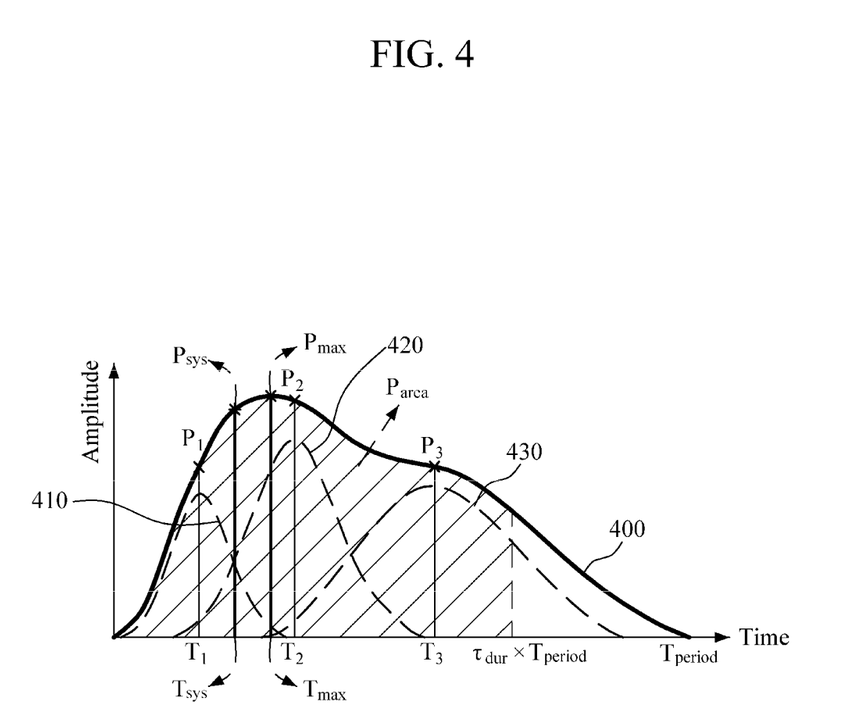
FIG. 4 is a graph for describing features of a photoplethysmorgram (PPG) signal for blood pressure trend tracking according to an example embodiment.

FIG. 4 is an example graph showing features of a PPG signal for blood pressure trend tracking.

A change in blood pressure may depend on, for example, a cardiac output, which represents the amount of blood ejected by the heart in a unit of time, and a total peripheral resistance. It may be expressed as Equation 1.

$$\Delta BP = CO \times TPR \quad (1)$$

$\Delta BP$ represents a blood pressure difference between the right and left ventricles, CO represents a cardiac output, and TPR represents a total peripheral resistance.

As the cardiac output or the total peripheral resistance increases, the blood pressure may also increase. Therefore, features of the PPG signal 400 may include a first feature which is highly correlated with the cardiac output and a second feature which is highly correlated with the total peripheral resistance. In this case, the first feature may be related to the amplitude of a feature point and the second feature may be related to the time of the feature point.

Referring to FIG. 4, a waveform of a PPG signal 400 may be a summation of a propagation wave 410 propagating from the heart to the peripheral parts of a body and reflection waves 420 and 430 returning from the peripheral parts of the body to the heart. That is, the PPG signal 400 may be a summation of three or more component pulses 410 to 430. In this case, reference numeral 400 denotes the PPG signal of one period $T_{period}$, 410 denotes a first component pulse, 420 denotes a second component pulse, and 430 denotes a third component pulse. In addition, $T_1$ denotes the time of the peak point of the first component pulse 410, $P_1$ denotes the amplitude of the PPG signal 400 at $T_1$, $T_2$ denotes the time of the peak point of the second component pulse 420, $P_2$ denotes the amplitude of the PPG signal 400 at $T_2$, $T_3$ denotes the time of the peak point of the third component pulse 430, $P_3$ denotes the amplitude of the PPG signal 400 at $T_3$, $T_{max}$ denotes the time of the peak point of the PPG signal 400 in a predetermined interval (a first interval), $P_{max}$ denotes the amplitude of the PPG signal 400 at $T_{max}$, $T_{sys}$ denotes the intermediate time between $T_1$ and $T_{max}$, $P_{sys}$ denotes the amplitude of the PPG signal 400 at $T_{sys}$, $\tau_{dur}$ denotes a setting factor ($(0 \leq \tau_{dur} \leq 1)$ (e.g., 0.7) of the system, and $P_{area}$ denotes the sum of amplitudes of the PPG signal 400 between time 0 and $\tau_{dur} * T_{period}$ (a second interval).

The first feature is a feature highly correlated with the cardiac output, that is, a feature related to the amplitude of a feature point, and may include, for example, $P_{max}/P_{area}$, $P_{max}/P_3$, $P_{sys}/P_3$, $P_1/P_3$, $P_2/P_3$, or the like.

The second feature is a feature highly correlated with the total peripheral resistance, that is, a feature related to the time of a feature point, and may include $1/(T_3-T_{sys})$, $1/(T_3-T_{max})$, $1/(T_3-T_1)$, $1/(T_3-T_2)$, or the like.

Meanwhile, $T_{sys}$ is shown as an intermediate time between $T_1$ and $T_{max}$ in FIG. 4, but embodiments are not limited thereto. For example, $T_{sys}$ may be any internally dividing point in time between $T_1$ and $T_{max}$ or any internally dividing point in time between $T_1$ and $T_2$.

Figure 5:
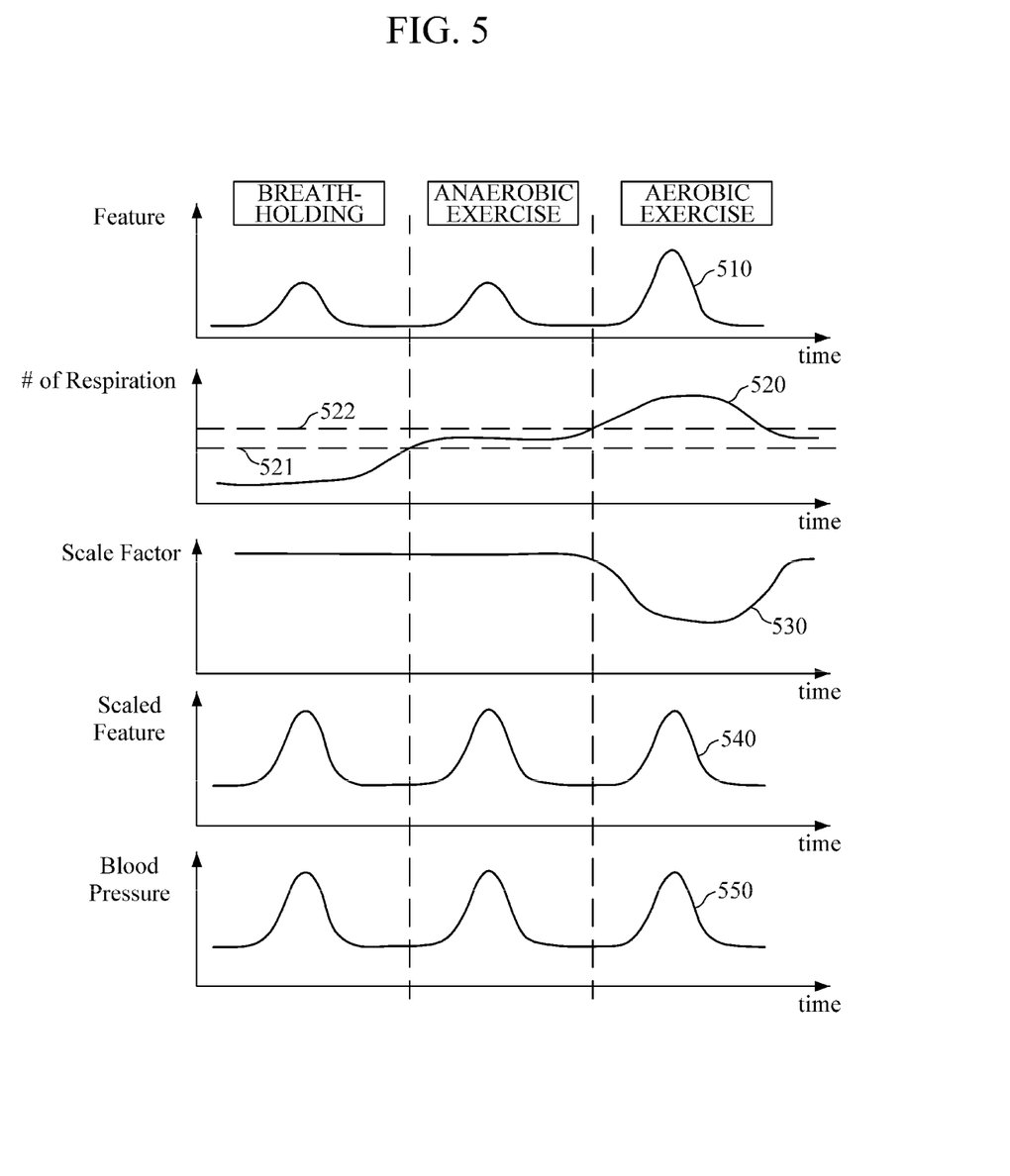
FIG. 5 illustrates graphs for describing a scale factor calibration method according to an example embodiment.

FIG. 5 illustrates example graphs for describing a scale factor calibration method. FIG. 5 shows an example in which a bio-signal is a PPG signal and a bio-state is a blood pressure.

Referring to FIGS. 3 and 5, the feature extractor 310 may extract a feature 510 which corresponds to the change in the blood pressure from the PPG signal of the object.

The bio-state change cause estimator 320 may measure the respiration rate 520 of the object and may estimate a cause of blood pressure change of the object using the respiration-cause relation model on the basis of the measured respiration rate 520. As shown in FIG. 5, when the respiration rate 520 is equal to or less than a first threshold 521, the bio-state change cause estimator 320 determines that the cause of blood pressure change is breath-holding; when the respiration rate 520 exceeds the first threshold 521 and is less than a second threshold 522, the bio-state change cause estimator 320 determines that the cause of blood pressure change is anaerobic exercise; and when the respiration rate 520 exceeds the second threshold 522, the bio-state change cause estimator 320 determines that the cause of blood pressure change is aerobic exercise.

The scale factor calibrator 330 may calibrate a scale factor using the cause-scale factor calibration relation model on the basis of the estimated cause of blood pressure change. As shown in FIG. 5, the scale factor calibrator 330 does not calibrate the scale factor 530 when the cause of blood pressure change is breath-holding or anaerobic exercise, and when the cause of blood pressure change is aerobic exercise, the scale factor calibrator 330 reduces the scale factor 530.

The feature scaler 340 scales the feature 510 by applying the calibrated scale factor 530 to the feature 510. Reference numeral 540 denotes a scaled feature.

As shown in FIG. 5, since the scaled feature 540 reflects the cause of blood pressure change, the scaled feature 540 corresponds to the change of blood pressure 550 according to each cause of blood pressure change.

Figure 6:
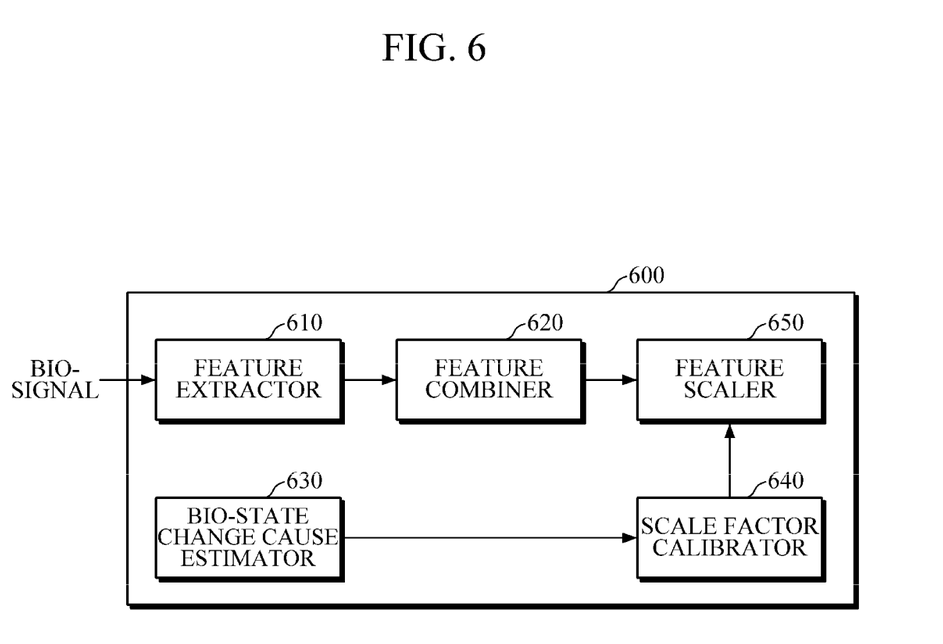
FIG. 6 is a block diagram illustrating a bio-signal feature scaling apparatus according to an example embodiment.

FIG. 6 is a block diagram illustrating a bio-signal feature scaling apparatus according to an example embodiment.

Referring to FIG. 6, the bio-signal feature scaling apparatus 600 may include a feature extractor 610, a feature combiner 620, a bio-state change cause estimator 630, a scale factor calibrator 640, and a feature scaler 650.

The feature extractor 610 may extract a plurality of features from a bio-signal of an object. In this case, as described with reference to FIG. 4, the features may include a first feature highly correlated with a cardiac output and a second feature highly correlated with a total peripheral resistance.

The feature combiner 620 may combine the plurality of extracted features. For example, the feature combiner 620 may apply different weights to the respective features and linearly combine the weight-applied features. In this case, the weights applied to the respective features may be experimentally or theoretically derived and stored in advance in an internal database or an external database of the bio-signal feature scaling apparatus 600.

The bio-state change cause estimator 630 may estimate a cause of change in the bio-state of the object, the scale factor calibrator 640 may calibrate a previously stored scale factor on the basis of the estimated cause of change in the bio-state, and the feature scaler 650 may scale the combined feature by applying the calibrated scale factor to the combined feature. The bio-state change cause estimator 630, the scale factor calibrator 640, and the feature scaler 650 correspond to the bio-state change cause estimator 320, the scale factor calibrator 330, and the feature scaler 340 of FIG. 3, respectively, and thus detailed descriptions thereof will be omitted.

Figure 7:
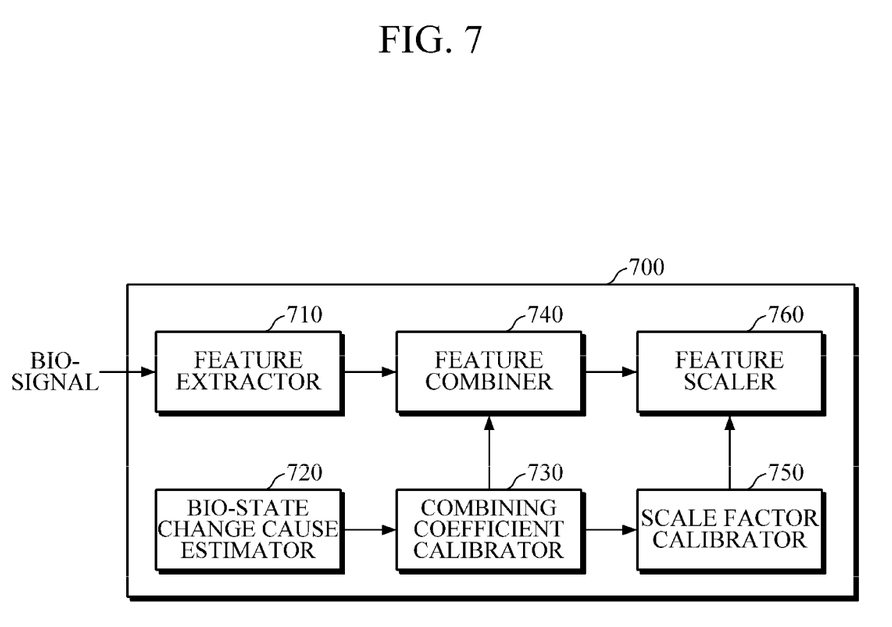
FIG. 7 is a block diagram illustrating a bio-signal feature scaling apparatus according to an example embodiment.

FIG. 7 is a block diagram illustrating a bio-signal feature scaling apparatus according to an example embodiment.

Referring to FIG. 7, the bio-signal feature scaling apparatus 700 may include a feature extractor 710, a bio-state change cause estimator 720, a combining coefficient calibrator 730, a feature combiner 740, a scale factor calibrator 750, and a feature scaler 760. In this case, the feature extractor 710, the bio-state change cause estimator 720, the feature combiner 740, the scale factor calibrator 750, and the feature scaler 760 correspond to the feature extractor 610, the bio-state change cause estimator 630, the feature combiner 620, the scale factor calibrator 640, and the feature scaler 650 of FIG. 6, respectively, and thus detailed descriptions thereof will be omitted.

The combining coefficient calibrator 730 may calibrate the different weights to be applied to the respective features on the basis of the cause of change in the bio-state which is estimated by the bio-state change cause estimator 720. According to an example embodiment, the combining coefficient calibrator 730 may calibrate the weights to be applied to the respective features using a model (cause-combining coefficient calibration relation model) which defines a relationship between the cause of change in the bio-state and the calibration of the combining coefficient. For example, when the cause of change in the bio-state is breath-holding, the combining coefficient calibrator 730 may reduce a weight of a first feature which is highly correlated with the cardiac output and increase a weight of a second feature which is highly correlated with the total peripheral resistance among the plurality of features. In addition, when the cause of change in the bio-state is aerobic exercise, the combining coefficient calibrator 730 may increase the weight of the first feature which is correlated with the cardiac output and reduce the weight of the second feature which is highly correlated with the total peripheral resistance among the plurality of features. Further, when the cause of change in the bio-state is anaerobic exercise, the bio-state change cause estimator 720 may reduce the weight of the first feature and increase the weight of the second feature, or increase the weight of the first feature and reduce the weight of the second feature according to the respiration rate. In this case, the adjustment amount of each weight may be determined based on the respiration rate.

Figure 8:
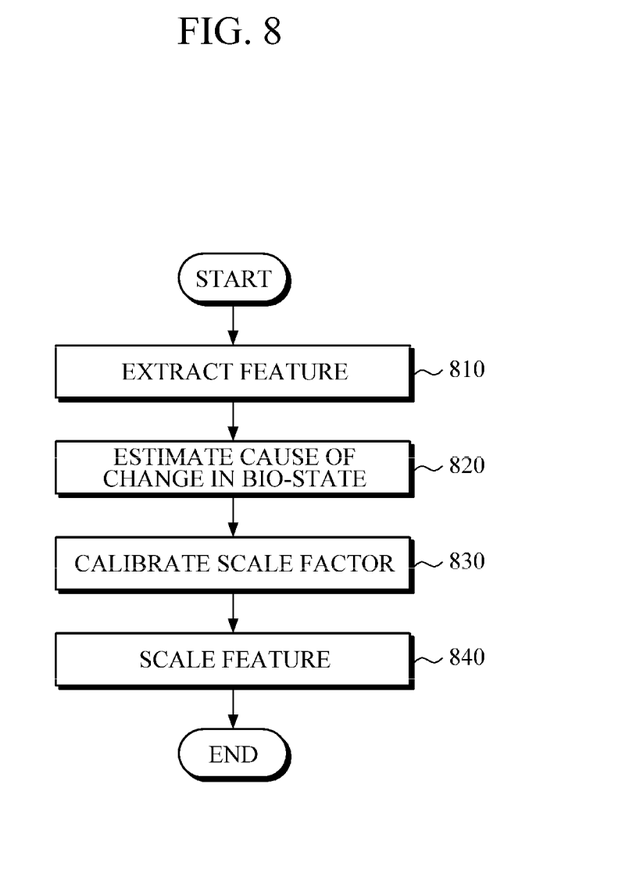
FIG. 8 is a flowchart illustrating a bio-signal feature scaling method according to an example embodiment.

FIG. 8 is a flowchart illustrating a bio-signal feature scaling method according to an example embodiment.

The bio-signal feature scaling method of FIG. 8 may be performed by the bio-signal feature scaling apparatus 300 of FIG. 3.

Referring to FIGS. 3 and 8, the bio-signal feature scaling apparatus 300 may extract a feature that follows the change of bio-state from a bio-signal of an object, as shown in 810. In this case, the bio-signal may be an electrical signal transmitted between cells in vivo and may include an ECG signal, a PPG signal, an EMG signal, a BCG signal, etc. In addition, the bio-state may include various vital signs including blood pressure.

The bio-signal feature scaling apparatus 300 may estimate a cause of change in the bio-state of the object, as shown in 820. According to an example embodiment, the bio-signal feature scaling apparatus 300 may measure a breathing pattern including a respiration rate of the object, and may estimate a cause of change in the bio-state on the basis of the measured breathing pattern. In this case, the bio-signal feature scaling apparatus 300 may estimate the cause of change in the bio-state using a respiration-cause relation model.

The bio-signal feature scaling apparatus 300 may measure the breathing pattern of the object using various methods.

According to an example embodiment, the bio-signal feature scaling apparatus 300 may directly measure the breathing pattern of the object using a respiration sensor attached to the object.

According to an example embodiment, the bio-signal feature scaling apparatus 300 may indirectly measure the breathing pattern of the object by analyzing a bio-signal, such as an ECG signal, a PPG signal, an EMG signal, or a BCG signal. For example, the bio-signal feature scaling apparatus 300 may indirectly measure the breathing pattern of the object by analyzing a low frequency fluctuation component, i.e., an amplitude component, or the heart rate or inter beat interval (IBI) obtained from the bio-signal.

According to an example embodiment, the bio-signal feature scaling apparatus 300 may measure the breathing pattern of the object using both the respiration sensor and the bio-signal.

The bio-signal feature scaling apparatus 300 may calibrate the previously stored scale factor on the basis of the cause of change in the bio-state, as shown in 830. According to an example embodiment, the bio-signal feature scaling apparatus 300 may calibrate the scale factor using the cause-scale factor calibration relation model.

The bio-signal feature scaling apparatus 300 may scale the feature by applying the calibrated scale factor to the feature, as shown in 840.

Figure 9:
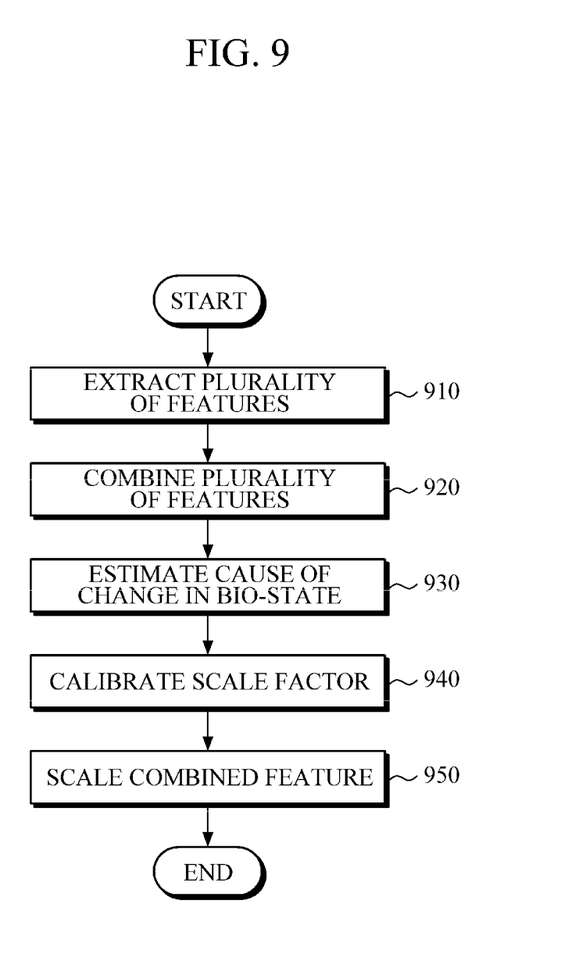
FIG. 9 is a flowchart illustrating a bio-signal feature scaling method according to an example embodiment.

FIG. 9 is a flowchart illustrating a bio-signal feature scaling method according to an example embodiment.

The bio-signal feature scaling method of FIG. 9 may be performed by the bio-signal feature scaling apparatus 600 of FIG. 6.

Referring to FIGS. 6 and 9, the bio-signal feature scaling apparatus 600 may extract a plurality of features that correspond to the change of bio-state from a bio-signal of an object, as shown in 910. In this case, as described with reference to FIG. 4, the features may include a first feature highly correlated with a cardiac output and a second feature highly correlated with a total peripheral resistance.

The bio-signal feature scaling apparatus 600 may combine the plurality of extracted features, as shown in 920. For example, the bio-signal feature scaling apparatus 600 may apply different weights to the respective features and linearly combine the weight-applied features.

The bio-signal feature scaling apparatus 600 may estimate a cause of change in the bio-state of the object, as shown in 930, calibrate a previously stored scale factor on the basis of the estimated cause of change in the bio-state, as shown in 940, and scale the combined feature by applying the calibrated scale factor to the combined feature, as shown in 950.

Figure 10:
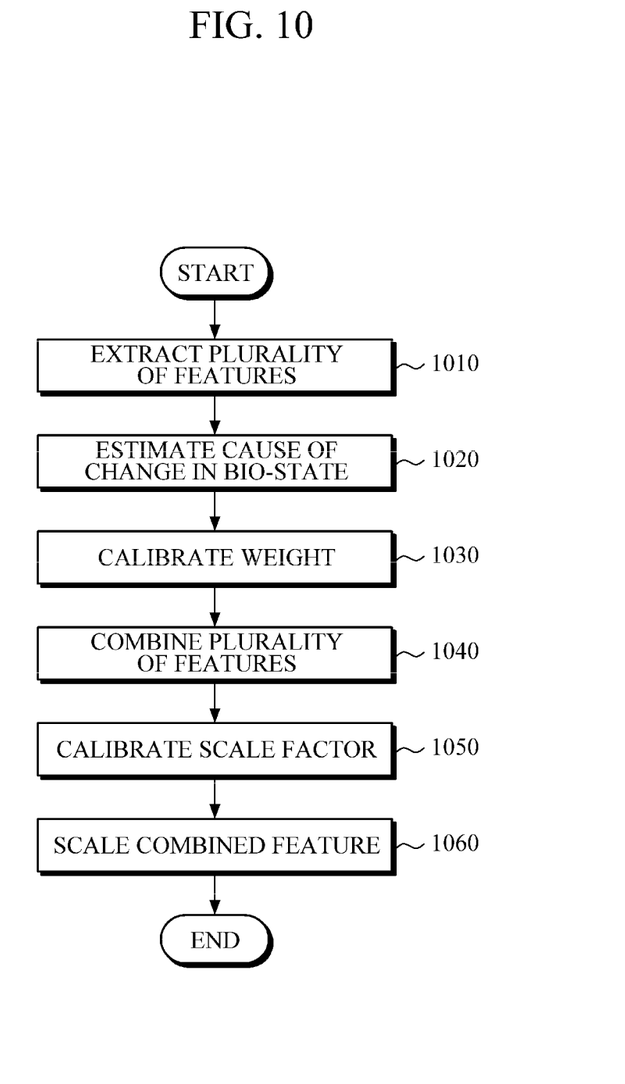
FIG. 10 is a flowchart illustrating a bio-signal feature scaling method according to an example embodiment.

FIG. 10 is a flowchart illustrating a bio-signal feature scaling method according to an example embodiment.

The bio-signal feature scaling method of FIG. 10 may be performed by the bio-signal feature scaling apparatus 700 of FIG. 7.

Referring to FIGS. 7 and 10, the bio-signal feature scaling apparatus 700 may extract a plurality of features that correspond to the change of bio-state from a bio-signal of an object, as shown in 1010.

The bio-signal feature scaling apparatus 700 may estimate a cause of change in the bio-state of the object, as shown in 1020. According to an example embodiment, the bio-signal feature scaling apparatus 700 may measure a breathing pattern including a respiration rate of the object, and estimate a cause of change in the bio-state on the basis of the measured breathing pattern. In this case, the bio-signal feature scaling apparatus 700 may estimate the cause of change in the bio-state using a respiration-cause relation model.

The bio-signal feature scaling apparatus 700 may calibrate different weights to be applied to the respective features on the basis of the estimated cause of change in the bio-state, as shown in 1030. According to an example embodiment, the bio-signal feature scaling apparatus 700 may calibrate the weights to be applied to the respective features using a cause-combining coefficient calibration relation model. For example, when the cause of change in the bio-state is breath-holding, the bio-signal feature scaling apparatus 700 may reduce a weight of a first feature which is highly correlated with the cardiac output and increase a weight of a second feature which is highly correlated with the total peripheral resistance among the plurality of features. In addition, when the cause of change in the bio-state is aerobic exercise, the bio-signal feature scaling apparatus 700 may increase the weight of the first feature which is highly correlated with the cardiac output and reduce the weight of the second feature which is highly correlated with the total peripheral resistance among the plurality of features. Further, when the cause of change in the bio-state is anaerobic exercise, the bio-signal feature scaling apparatus 700 may reduce the weight of the first feature and increase the weight of the second feature, or increase the weight of the first feature and reduce the weight of the second feature according to the respiration rate. In this case, the adjustment amount of each weight may be determined based on the respiration rate.

The bio-signal feature scaling apparatus 700 may combine the plurality of features by applying the different calibrated weights to the respective features, as shown in 1040.

The bio-signal feature scaling apparatus 700 may calibrate a previously stored scale factor on the basis of the estimated cause of change in the bio-state, as shown in 1050, and may scale the combined feature by applying the calibrated scale factor to the combined feature, as shown in 1060.

The example embodiments may be implemented with, for example, a processor and instructions such as computer readable codes stored in a computer readable record medium. When the instructions are executed by one or more processors, the one or more processors may perform a function corresponding to the instructions. The computer readable record medium includes all types of record media in which computer readable data are stored. Examples of the computer readable record medium may include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

Example embodiments have been described above. Nevertheless, the exemplary embodiments are not limited thereto, and various modifications may be made without departing from the gist and scope of the present disclosure as described by the appended claims, and their equivalents.

What is claimed is:

1. A bio-signal feature scaling apparatus comprising:
a processor configured to execute instructions to:
extract a first feature from a photoplethysmogram (PPG) signal of an object, the PPG signal being correlated to a blood pressure of the object;
extract a second feature that is different from the first feature from the PPG signal of the object;
estimate a cause of a change in the blood pressure of the object;
calibrate a first weight and a second weight to be applied to the first feature and the second feature, respectively, based on the estimated cause of the change in the blood pressure;
combine the first feature and the second feature into a combined feature by applying the calibrated weights to the respective features;
calibrate a scale factor that is a ratio between a change in the combined feature to the change in the blood pressure based on the estimated cause of the change in the blood pressure; and
scale the combined feature by applying the calibrated scale factor to the combined feature.

2. The bio-signal feature scaling apparatus of claim 1, wherein the cause of change in the blood pressure comprises at least one from among breath-holding, anaerobic exercise, aerobic exercise, and stress.

3. The bio-signal feature scaling apparatus of claim 1, wherein the processor is further configured to measure a breathing pattern comprising a respiration rate of the object and estimate the cause of change in the blood pressure based on the measured breathing pattern.

4. The bio-signal feature scaling apparatus of claim 3, wherein the processor is further configured to measure the breathing pattern of the object using a respiration sensor attached to the object.

5. The bio-signal feature scaling apparatus of claim 3, wherein the processor is further configured to measure the breathing pattern of the object by analyzing the PPG signal.

6. The bio-signal feature scaling apparatus of claim 5, wherein the processor is further configured to measure the breathing pattern of the object by analyzing at least one from among a heart rate or inter beat interval (IBI) obtained from the PPG signal, or analyzing a low frequency fluctuation component comprising an amplitude component of the PPG signal.

7. The bio-signal feature scaling apparatus of claim 1, wherein the processor is further configured to calibrate the scale factor based on a model that defines a relationship between a cause of change in the blood pressure and calibration of the scale factor.

8. A bio-signal feature scaling method comprising:
extracting a first feature from a photoplethysmogram (PPG) signal of an object, the PPG signal being correlated to a blood pressure of the object;
extracting a second feature that is different from the first feature from the PPG signal of the object;
estimating a cause of a change in the blood pressure of the object;
calibrating a first weight and a second weight to be applied to the first feature and the second feature, respectively, based on the estimated cause of change in the blood pressure;
combining the first feature and the second feature into a combined feature by applying the calibrated weights to the respective features;
calibrating a scale factor that is a ratio between a change in the combined feature to the change in the blood pressure based on the estimated cause of the change in the blood pressure; and
scaling the combined feature by applying the calibrated scale factor to the combined feature.

9. The bio-signal feature scaling method of claim 8, wherein the cause of change in the blood pressure comprises at least one from among breath-holding, anaerobic exercise, aerobic exercise, and stress.

10. The bio-signal feature scaling method of claim 8, wherein the estimating of the cause of change in the blood pressure comprises measuring a breathing pattern comprising a respiration rate of the object and estimating the cause of change in the blood pressure based on the measured breathing pattern.

11. The bio-signal feature scaling method of claim 10, wherein the measuring of the breathing pattern comprises measuring the breathing pattern of the object using a respiration sensor attached to the object.

12. The bio-signal feature scaling method of claim 10, wherein the measuring of the breathing pattern comprises measuring the breathing pattern of the object by analyzing the PPG signal.

13. The bio-signal feature scaling method of claim 10, wherein the measuring of the breathing pattern comprises measuring the breathing pattern of the object by analyzing at least one from among a heart rate or inter beat interval (IBI) obtained from the PPG signal, or analyzing a low frequency fluctuation component comprising an amplitude component of the PPG signal.

14. The bio-signal feature scaling method of claim 8, wherein the calibrating of the scale factor comprises calibrating the scale factor based on a model that defines a relationship between a cause of change in the blood pressure and calibration of the scale factor.

15. A bio-signal feature scaling apparatus comprising:
a processor configured to execute instructions to:
extract a plurality of features from a photoplethysmogram (PPG) signal of an object, the PPG signal being correlated to a blood pressure of the object, the plurality of features comprising at least two types of features;
estimate a cause of a change in the blood pressure of the object;
calibrate weights to be applied to the plurality of features, respectively, based on the estimated cause of change in the blood pressure;
combine the plurality of features by applying the calibrated weights to the respective features;
calibrate a stored scale factor that is a ratio between a change in the combined plurality of features to the change in the blood pressure based on the estimated cause of change in the blood pressure; and
scale the combined plurality of features by applying the calibrated scale factor to the combined plurality of features.

16. The bio-signal feature scaling apparatus of claim 15, wherein the processor is further configured to measure a breathing pattern comprising a respiration rate of the object and estimate the cause of change in the blood pressure based on the measured breathing pattern.

17. The bio-signal feature scaling apparatus of claim 15, wherein the processor is further configured to calibrate the weights to be applied to the features, respectively, by using a model that defines a relationship between a cause of change in the blood pressure and calibration of a combining coefficient.

* * * * *